US006939679B1

(12) United States Patent
Sato et al.

(10) Patent No.: US 6,939,679 B1
(45) Date of Patent: Sep. 6, 2005

(54) NADE BINDING PROTEINS

(75) Inventors: Takaaki Sato, Tokyo (JP); Shinji Irie, Ibaraki (JP)

(73) Assignee: Riken, Saitama (JP)

( * ) Notice: Subject to any disclaimer, the term of this patent is extended or adjusted under 35 U.S.C. 154(b) by 7 days.

(21) Appl. No.: 09/661,305

(22) Filed: Sep. 13, 2000

(30) Foreign Application Priority Data

Sep. 14, 1999 (JP) .......................................... 11/260947

(51) Int. Cl.[7] .............................................. G01N 33/543

(52) U.S. Cl. ............................... 435/7.1; 435/4; 435/6; 436/501; 436/518

(58) Field of Search ...................... 435/7.1, 4; 436/501, 436/518, 7.23; 530/350, 358

(56) References Cited

FOREIGN PATENT DOCUMENTS

| | | |
|---|---|---|
| EP | 0841399 | 5/1998 |
| WO | 95/51544 | 11/1995 |

OTHER PUBLICATIONS

Brown et al (1999, Human Molecular Genetics vol. 8, pp. 611–619).*
Rabizadeh, S., et al., Science, 261, pp. 345–348 (1993).
Frade, J., et al., Nature, 383, pp. 166–168 (1996.
Barrett, G. and Bartlett, P., et al., Proc. Natl. Acad. Sci., 91, pp. 6501–6505 (1994).
Mukai, J., et al., J. Biol. Chem., 257, pp. 17566–17570 (2000).
Casha, S., et al., Neuroscience, 103, pp. 203–218 (2001).
Park, J., et al., J. Neuroscience, 20, pp. 9096–9103 (2000).
Rabizadeh, S., et al., Proc. Natl. Acad. Sci., 91, pp. 10703–10706 (1994).
Yaar, M., et al., J. Clin. Invest., 100, pp. 2333–2340 (1997).
Kimura, M, et al., J. Biol. Chem., 276, pp. 17291–17300 (2001).
Fanburg–Smith, J. and Miettinen, M., Human Pathology, 32, 976–983 (2001).
Descamps, S., et al., Cancer Res., 61, pp. 4337–4340 (2001).
Mukai, J., et al., Biol. Chem., 275, 17566–17570 (2000).
Brown, A. and Kay, G., Human Molec. Genet., 8, 611–619 (1999).
Ichimura, T., et al., Proc. Natl. Acad. Sci., 85, 7084–7088 (1988).
Isobe, T., et al., J. Mol. Biol., 217, 125–132 (1991).
Igaku, Jiken, Experimental Medicine, 13:6, 120–125 (1995).
Su, Y., et al.,.EMBO, 16:6, 1279–1290 (1997).
Yao, Z., et al., J. Biol. Chem., 274:4, 2118–2125 (1999).
Oren, M., Nature, 391, 233–234 (1998).
Garkavtsev, I., et al., Nature, 391, 295–298 (1998).
Helbing, C., et al., Cancer Research, 57, 1255–1258 (1997).
Imataka, H., et al., EMBO, 16:4, 817–825 (1997).
Yamanaka, S., et al., Genes and Dev., 11, 321–333 (1997).
Igaku, J., Experimental Medicine, 17:7, 862–864 (1999).
Imataka, H. and Sonenburg, N., Molec. Cell Biol., 17:12, 6940–6947 (1997).
Tarun, S., et al., Proc. Natl. Acad. Sci., 94, 9046–9051 (1997).
Imataka, H., et al., EMBO, 17:24, 7480–7489 (1998).
Wells, S., et al., Molec. Cell, 2, 135–140 (1998).
Kalchman, M., et al., Nature Genetics, 16, 44–53 (1997).
Vojtek, A., et al., Cell, 74, 205–214 (1993).
MacEwan, D., et al., Chemical Abstracts, vol. 124, No. 9, (Feb. 26, 1996).
MacEwan, Chemical Abstract, vol. 124, No. 9, Abstract No. 124:15129v.

* cited by examiner

*Primary Examiner*—Larry R. Helms
*Assistant Examiner*—Misook Yu
(74) *Attorney, Agent, or Firm*—Greenblum & Bernstein, P.L.C.

(57) ABSTRACT

Agents for use in screening of medicaments for treatment, prevention and/or diagnosis of apoptosis associated diseases are provided which comprise an apoptosis related protein binding to NADE ($p76^{NTR}$-associated cell death executor) or a DNA encoding said protein.

1 Claim, No Drawings

NADE BINDING PROTEINS

TECHNICAL FIELD

The present invention relates to agents for use in the screening of medicaments for treatment, prevention and/or diagnosis of diseases with cell apoptosis, a method for screening medicaments by using the agents, and medicaments selected by carrying out the screening.

BACKGROUND ART

Cell death plays an important role in every sort of life phenomenon. In particular, research on cell death in the nervous system is expected as useful to reveal general mechanism of cell death, as well as to develop therapeutic and preventive treatment of diseases relating to the brain and nerve which will presumably be more increasing in the future due to the presently progressing aging society.

The relationship between cell death and information transfer pathway has been being elucidated very recently. Especially as for Fas (CD95), TNF receptors and the like, various molecules have been isolated and identified which participate in information transfer starting from signal receptors of cell death and leading to caspase, a protein that executes cell death.

In nerve cells, information on proliferation and differentiation is transferred through the nerve growth factor (NGF), and it has become apparent recently that NGF induces cell death in some cells. Namely, it has been reported that NGF promotes nerve cell survival through the trkA receptor as a high-affinity receptor, whilst NGF induces cell death in immature nerve cells expressing only $p75^{NTR}$ as a low-affinity NGF receptor and mature neuroglia cells such as oligodendrocyte. $p75^{NTR}$ belongs to the TNF receptor superfamily from a viewpoint of structural feature, and has the death domain in its molecule similarly to TNF receptor. However, as to $p75^{NTR}$, participation of information transfer protein such as FADD and TRADD has not been reported, and information transfer to apoptosis has not yet been clearly revealed. The nerve growth factor (NGF) acts on cells of the nervous system and induces signals for cell survival, cell death or cell differentiation. Two receptors, i.e., a high-affinity nerve growth factor receptor (trkA) and a low-affinity one ($p75^{NTR}$), are known as NGF receptors. However, signal transfer mechanism mediated by $p75^{NTR}$ and molecules participating in the signal transfer have not yet been elucidated sufficiently.

With the progress of study on the signal transfer mechanism mediated by $p75^{NTR}$, a protein referred to as NADE ($p75^{NTR}$-associated cell death executor, referred to as "NADE"hereinafter in the specification) was first identified by the research group of Columbia University as a protein which binds to the nerve growth factor receptor ($p75^{NTR}$) and participates in the induction and regulation of apoptosis (Biol. Chem., 275, pp.17566–17670). It is known that NADE has 124 amino acids in the full length sequence and encodes a protein having the molecular weight of approximately 15 kDa (Hum. Mpl. Genet., 8, 611–619, 1999 reported as Bex8), and that NADE is highly expressed in the brain, heart and lung observed from mRNA level.

As described above, NADE has been elucidated to bind to the nerve growth factor receptor ($p75^{NTR}$) and participate in the induction and regulation of apoptosis. Identification of a protein which binds to NADE and associates with apoptosis mediated by NADE is expected to be useful for developing medicaments for treatment, prevention and/or diagnosis of apoptosis-associated diseases. However, such proteins have not been identified so far.

DISCLOSURE OF THE INVENTION

An object of the present invention is to identify a NADE-binding protein. Another object of the present invention is to elucidate the relationship between the identified NADE-binding protein and apoptosis-associated diseases. Other object of the present invention is to provide a method for screening medicaments for treatment, prevention and/or diagnosis of apoptosis-associated diseases by using the identified NADE-binding protein.

In order to achieve the foregoing objects, the inventors of the present invention first isolated cDNAs of various proteins that bound to NADE by means of the yeast two-hybrid system to clarify signal transfer pathway of apoptosis mediated by $p75^{NTR}$/NADE. As a result, the inventors successfully identified several interesting proteins including 14-3-3 gene product which is presumed to be an adaptor molecule participating in the intracellular information transfer, NIK (Nck interacting kinase) and the like, which bind to NADE and are suggested to be involved in apoptosis mediated by $p75^{NTR}$. The present invention was achieved on the basis of the findings.

According to one aspect of the present invention, there are thus provided agents for use in screening of medicaments for treatment, prevention and/or diagnosis of apoptosis-associated diseases which comprise an apoptosis-related protein which binds to NADE or a DNA encoding said protein.

The apoptosis-related proteins that bind to NADE include, for example, a protein selected from the group consisting of 14-3-3 protein, NIK/HGK protein, P33 ING relative protein, eIF4G protein and Huntingtin-binding protein 1.

According to another aspect of the present invention, there is provided a method for screening medicaments for treatment, prevention and/or diagnosis of apoptosis-associated diseases which comprises the step of detecting interaction between NADE and the apoptosis-related protein which binds to NADE in the presence of a medicament to be tested.

According to a preferred embodiment of the screening method of the present invention, when the tested medicament has an effect on the interaction between NADE and the apoptosis-related protein which binds to NADE, the medicament is chosen as a candidate of an effective medicament.

According to an embodiment of the screening method of the present invention, there is provided a method which comprises the steps of:

(a) subjecting NADE and the apoptosis-related protein which binds to NADE to interaction with each other in the presence of a medicament to be tested, (b) subjecting NADE and the apoptosis-related protein which binds to NADE to interaction with each other in the absence of the medicament to be tested, (c) detecting the interactions in the steps (a) and (b), and (d) comparing the interactions in the steps (a) and (b), and if the medicament has an effect on said interaction, the medicament is chosen as a candidate of an effective medicament.

According to other aspect of the present invention, there are provided medicaments for treatment, prevention and/or diagnosis of apoptosis-associated diseases which are chosen by the screening method of the present invention.

According to the present invention, it becomes possible to design medicaments controlling apoptosis and develop screening systems for the medicament. It can be expected to develop novel class of medicaments for various nervous diseases caused by abnormal regulation of apoptosis which are not available to date.

Best Mode for Carrying Out the Invention

The agents for use in screening of medicaments for treatment, prevention and/or diagnosis of apoptosis associated diseases according to the present invention are characterised to comprise an apoptosis-related protein which binds to NADE or a DNA encoding the protein.

The apoptosis-associated diseases herein used include any diseases associated with abnormal apoptosis such as those caused by apoptosis depression or acceleration, and those with depressed or accelerated apoptosis as a result of the disease.

Specific examples of the apoptosis-associated disease include, but not limited thereto, viral diseases such as AIDS, ARC (AIDS associated disease), adult T cell leukemia, ciliary cell leukemia, myelosis, respiratory disorders, arthrosis, HIV or HTLV-1 associated diseases including uveitis, and hepatitis C; cancers; collagen diseases such as systemic lupus erythematosus and chronic rheumatoid arthritis; autoimmune diseases such as ulcerative colitis, Sjogren's syndrome, primary biliary cirrhosis, sudden thrombocytopenic purpura, autoimmune hemolytic anemia, myasthenia gravis, and insulin dependent (type I) diabetes melitus; various diseases with thrombocytopenia such as osteomyelodysplasia syndrome, cyclic thrombocytopenia, aplastic anemia, sudden thrombocytopenia, and disseminated intravascular coagulation; liver diseases of viral or drug hepatitis such as types C, A, B and F, and hepatic cirrhosis dementia such as Alzheimer's disease and senile dementia of Alzheimer type cerebrovascular disorders; cardiovascular disorders nerve degeneration diseases adult respiratory distress syndrome; infectious diseases prostatic hypertrophy uterus myoma; bronchial asthma; arteriosclerosis various congenital malformation; nephritis; senile cataract; chronic fatigue syndrome; myodystrophy; peripheral nerve disorders; gastrointestinal disorders such as diarrhea and dysentery; eye disorders; obesity; depilation stress and ageing. The term "disease"herein used covers a broadest sense including physical and physiologic conditions such as obesity, depilation, stress and aging.

The apoptosis-associated diseases may be divided more specifically into diseases caused by apoptosis depression and those caused by apoptosis acceleration as follows.

The diseases caused by apoptosis depression include cancers such as follicular lymphoma, cancer caused by variation of p53, breast cancer, ovarian cancer and prostatic cancer autoimmune diseases such as systemic lupus erythematosus and immunity associated glomerulonephritis; and viral infections such as those caused by herpes virus, adenovirus, and poxvirus. The diseases caused by apoptosis acceleration include AIDS, nerve degeneration diseases such as Alzheimer's disease, Parkinson's disease, amyotrophic lateral sclerosis, pigmentous retinitis and cerebellar degeneration; ischemic diseases such as myocardial infarction and cerebral apoplexy osteomyelodysplasia diseases such as aplastic anemia and toxic diseases such as alcoholic hepatitis.

NADE has been reported to bind to the nerve growth factor receptor ($p75^{NTR}$) ; and participate in the induction and regulation of apoptosis as described above, and its amino acid sequence and the base sequence encoding the protein are known (Hum, Mpl. Genet., 8, 611–619, 1999 reported as Bex3; its entire disclosure is incorporated herein by reference). NADE protein contains 124 amino acids in its full length and has the molecular weight of approximately 15 kDa. NADE is found to be highly expressed in the brain, heart and lung observed from the mRNA level.

The term "apoptosis-related protein which binds to NADE" herein used means any one of proteins which bind to NADE and participate in apoptosis, which includes unknown as well as known proteins. Preferably, the apoptosis-related protein according to the present invention are proteins whose abnormal interaction with NADE relates in any degree to apoptosis-associated diseases in the intracellular signal transfer pathway via $p75^{NTR}$/NADE complex.

Specific examples of such apoptosis related protein include, but not limited thereto, the following proteins. References of the proteins will be given in parentheses and all of the disclosures thereof are incorporated herein by reference.

(1) 14-3-3 Protein (Ichimura, T. et al., Proc. Natl. Acad. Sci. USA, 85:7084–7088, 1988 Isobe, T. et al., J. Mol. Biol., 217: 125–132, 1991; and Jikken Igaku (Experimental Medicine) Vol. 13, No. 6 (extra number) 1996, p.120–125, and references therein described).

As functions thereof, those in the intranuclear and extranuclear signal transfer systems have been presumed, which mainly includes control of proliferation and differentiation signals which connect to receptor tyrosine kinases such as EGF (fibroblast growth factor), PDGF (platelet-derived growth factor) and insulin, as well as $Ca^{2+}$ signal control through $Ca^{2+}$-calmodulin dependent protein kinase II and $Ca^{2+}$-phospholipid dependent protein kinase as major kinases, and also includes regulations of blood coagulation signals, the $H^+$ transfer system and transcriptions mediated by Gbox element.

(2) NIK/HGK Protein (Yi-Chi Su et al., The EMBO Journal, Vol. 16, No. 6, pp. 1279–1290, 1997; and Zhengbin Yao et al., The Journal of Biological Chemistry, Vol. 274, No. 4, pp. 2118–2125, 1999)

NIK/HGK functions as an upstream factor MAPKKKK in MAPK cascade to regulate the activity of JNK or P38MAPK through phosphorylation of MEKK and TAX. Recently, different groups have reported that JNK participates in the apoptosis regulation signal mechanism, suggesting that NIK/HGK participates in apoptosis induced by NGF/ $p75^{NTR}$.

(3) P33 ING1 Protein (Moshe Oren, Nature, Vol. 391, p.233–234, 1998; Igor Garkavtseve et al., Nature, Vol. 391, p.295–298, 1998; and Caren C. Helbing et al., Cancer Research 57,1255–1258, 1997)

P33 ING1 is a candidate of a cancer repressor gene. P33ING1 is considered to be one of factors constituting the p53 signal transfer pathway which represses cell proliferation in combination with p53 by controlling activation of p53 dependent transcription. Apoptosis relating to cell cycle may possibly be regulated through ING1.

(4) eIF4G Protein (Imataka, H. et al., EMBO Journal, 16, 817–825, 1997; Yamanaka, S. et al., Genes & Dev., 11: 321–333, 1997; and Jikken Igaku (Experimental Medicine) Vol. 17, No. 7(May), 1999 and references cited therein)

eIF4G is a translation initiator which binds to proteins connecting to the 3'- and 6'-terminals of mRNA (PABP: poly A binding protein, eIF4E: binding to CAP structure) to capture mRNA, and gather ribosomes and lead to translation initiation. The translation regulation through NADE/eIF4G may possibly control apoptosis.

(5) Huntingtin binding protein 1 (HIP1) (Michael A. Kalchman et al., Nature Genetics, Vol, 16, p.44–p.63, 1997)

This protein is expressed specifically in the cerebrum and cerebellum (no HIP1 protein expression in skeletal muscle, heart, testis, kidney, spleen, liver, and lung), and binds to huntingtin which is a gene product causing Huntington's chorea. HIP1 has homology to Sla2p and Sla2c of yeast S, cerevisiae (cytoskeltal-associated protein) and 2K370.3 of C. elegans, suggesting that HIP1 participates in apoptosis control through regulation of cytoskeleton formation.

The origins of the apoptosis-related proteins that bind to NADE used in the present invention are not limited, and the proteins may be any proteins such as naturally-derived, recombinant, and chemically synthesized proteins.

The apoptosis-related proteins that bind to NADE used in the present invention may be in the form of those added with a reactive substance, a labeling substance or the like to facilitate subsequent detection steps and the like so that the protein can be suitably used as an agent for screening.

As the agent of the present invention, a DNA encoding the apoptosis-related protein which binds to NADE may be used, in addition to the protein, per se. The apoptosis-related protein is expressed in cells by transfection of a recombinant vector to the cells, which is prepared by ligating a DNA encoding the apoptosis-related protein to a suitable expression vector, and then interaction between the protein thus expressed and NADE can be assayed to screen medicaments for treatment, prevention and/or diagnosis of apoptosis-associated diseases. The expression vector to express a DNA encoding the apoptosis-related protein can be appropriately selected by persons of ordinary skill in the art depending on types of the DNA and the like. In general, the expression vector comprises an appropriate promoter sequence, and if necessary, an appropriate selection marker gene and the like.

The present invention also relates to a method for screening medicaments for treatment, prevention and/or diagnosis of apoptosis-associated diseases which comprises the step of detecting g an interaction between NADE and an apoptosis-related protein which binds to NADE in the presence of a medicament to be tested.

The interaction between NADE and the apoptosis related-protein binding to NADE sea protein-protein interaction. Methods for detecting such protein-protein interactions are known in the field, and persons of ordinary skill in the art can appropriately use any method. For example, the following methods can be used.

(1) Coprecipitation (Immune precipitation)

Methods for coprecipitation are known, and an example will be given in Examples of the specification. For example, an agent of the present invention is mixed with NADE in an appropriate solution in the presence of a medicament to be tested in various concentrations to allow interactions with each other, and then the complex of the agent and NADE is subjected to coprecipitation. Then, the precipitate is immunoblotted and then detected using antibodies suitable for detecting the complex (the detection can be NADE by using anti-NADE antibody and the like as the primary antibody, and the secondary antibody which reacts with the primary antibody), by which effects of the tested medicament on the interaction between NADE and the apoptosis related protein which binds to NADE can be investigated. The effects of the test medicament on the interaction may be either direct or indirect, and their modes are not limited.

(2) ELISA

By fixing the NADE protein on a carrier such as a plate, a nylon filter and a nitrocellulose filter, inhibition or promotion of the binding with the labeled NADE binding protein can be monitored. Alternatively, by fixing the NADE binding protein on a plate, inhibition or promotion of the binding with the labeled NADE protein may be monitored. As the compounds to be screened, chemical libraries and the like can be used, (3) Application of the yeast two-hybrid system By simultaneously expressing NADE and the NADE binding protein in yeast and then transducing cDNA or a peptide library to the cells, yeast clones can be screened which have a cDNA effecting the interaction of NADE the NADE binding protein. A compound of a low molecular weight can be designed in view of the resulting amino acid sequence.

(4) Use of animal cells

By using a reporter gene whose activity in animal cells is easily determined such as CAT and luciferase, a system (cells) is constructed that has activity when interaction between NADE and the NADE binding protein exists. To the cells, a cDNA, a peptide library, or a low-molecular weight chemical library having high cell membrane permeability is added, and then a substance which effects the interaction of NADE/the NADE binding protein is screened by observing alteration in expression of the reporter gene.

NADE and the apoptosis-related protein which binds to NADE used in the screening method of the present invention may be added to the assay system in the forms of proteins, or supplied to the assay system in the forms of DNAs integrated into expression vectors and the like and expressed in the assay system.

The order to add NADE and the apoptosis-related protein which binds to NADE is not limited, in either way of addition in the forms of proteins or in the forms of DNAs, and they may be added simultaneously or one of them may be added in advance.

The effect of the tested medicament on the interaction between NADE and the apoptosis-related protein which binds to NADE is preferably determined in comparison with a control in which the tested medicament is not added. In addition, it is preferred to investigate whether or not the effects on the interaction change dose dependently by changing amounts of the tested medicament, and to investigate alteration of the effects on the protein-protein interaction with time by a continuous assay.

If the tested medicament has an effect on the interaction between NADE and the apoptosis-related protein which binds to NADE (the effect includes any of advancement or reduction of the interaction, which to be chosen may depend on the type of the apoptosis-related protein used and that of a disease to be treated by the tested medicament), the tested medicament can be chosen as a candidate of an effective medicament. The medicament thus chosen can be subjected to further examinations to verify its efficacy.

The present invention further relates to medicaments for treatment, prevention and/or diagnosis of apoptosis-associated diseases which are selected by the aforementioned screening method.

The types of the medicaments are not particularly limited, and examples include any types of medicaments such as cytokines, small-molecular medicaments including cell permeable small-molecular medicaments and the like, hormones, combinations of interleukin, lectin and another stimulator, specific antibodies, imitative peptides, antisense oligonucleotides, and other medicaments altering cell functions or protein expression.

The present invention also related to medicaments for treatment, prevention and/or diagnosis of apoptosis-associated diseases which comprise as an active ingredient a substance controlling intracellular expression or amount of the apoptosis-related protein which binds to NADE. Such medicaments include substances controlling transcription or translation of a gene of the apoptosis-related protein, antisense oligonucleotides of the gene, antibodies recognizing the protein (especially monoclonal antibodies) and the like.

EXAMPLES

The present invention will be explained more specifically with reference to the following examples. However, the scope of the present invention is not limited to the following examples.

Example 1

Identification of NADE Binding Protein Molecules by Yeast Two-Hybrid Method

Identification of NADE binding protein molecules was performed by yeast two-hybrid method modified by Dr. Stan Horenberg et al. (Cell, 74, 206–214, 1993). In L40 yeast cells (MATa his3 trpl leu2 ade2 LYZ2::]exA-HIS3 URA3::]exA-lacZ), each of lexA protein having DNA binding ability and VP 16 having transcription activating ability does not have transcription activity as a sole. However, the protein complex resulting from the binding between the proteins fusing with each domain induces transcription of reporter genes. That is, only when a fusion target protein of lexA and protein "X"and a fusion protein of VP16 and protein "Y"form a complex through the binding of X and Y, transcription levels of HIS3 and LacZ of reporter genes increase. Yeast cells having the lexA-X fusion protein and the VP16-Y fusion protein, and also having increased transcription of the reporter genes can be selected by observing recovery of a histidine requirement and determining β-galactosidase activity.

By means of this system, screening of a cDNA library derived from 9-days embryo of VP 16 fused mice was carried out by using NADE-lexA fusion protein as a target protein.

(1) Transformation of yeast L40 with recombinant vector having NADE gene

A full length NADE gene used for preparation of a recombinant vector was amplified and isolated by the PCR technique using mouse fetal cDNA (Clontech) as a template DNA, and ATGGATCCTCATGGCCAATGTCCACCAGC Seq. ID No: 1 and ATCTCGAGTCAAGGCATAAGGCAGAATTCATC Seq. ID No: 2 as primers. The resulting PCR product was treated with restriction enzymes of BamHI and Xhol, and ligated with expression vector pBTM116 which was treated beforehand with restriction enzymes of BamHI and SalI and with SAP to prepare recombinant vector pBTM116-NADE.

Then, yeast L40 cells were transformed by using the recombinant vector pBTMI16-NADE. A yeast L40 strain was cultured in 50 ml of YPD medium at 30° C. overnight. On the day of transformation, 10 ml of the culture solution was inoculated in 100 ml of YPD medium in a 500 ml flask, and cultured at 30° C. for 4 to 6 hours until $OD_{600}$ became 0.3 to 0.5. Then, the culture solution was centrifuged at 3,000 rpm at room temperature for 5 minutes, and the supernatant was removed. The cell pellet was washed with distilled water 3 times and then suspended in 4 ml of 0.1 M lithium acetate/1XTE, and the cells were allowed to stand et room temperature for 10 minutes. The resulting cells were used as competent cells.

The recombinant vector pBTM116-NADE (1 μg) and 100 μg of denatured salmon sperm DNA were placed in an Eppendolf tube and subjected to Vortex mixing. To the resulting mixture, 100 μl of the competent cell solution was added, and the mixture was gently stirred. In addition, 600 μl of 40% PEG3350/0.1 M lithium acetate/1 XTE was added to the Eppendolf tube, and the mixture was subjected to Vortex mixing and then allowed to stand at 30° C. for 30 minutes. After addition of 10 μl of DMSO and stirring, the mixture was treated at 42° C. for 16 minutes with stirring and then cooled. The tube was centrifuged at 16,000 rpm for 5 seconds and the supernatant was removed, and then the cell pellet was suspended in 500μl of TE.

The cell suspension above was spread over a plate of an essential medium without tryptophan (SD medium) and cultured at 30° C. to obtain a transformed cells having the recombinant vector pBTM116-NADE.

Expression of NADE in the transformants was examined in the following manner. The culture solution was first centrifuged at 3,000 rpm at room temperature for 10 minutes, and the pellet was washed with cold distilled water and centrifuged at 3,000 rpm at room temperature for 10 minutes. The pellet was suspended in 1 ml of cool distilled water and transferred into a tube of 1.5 ml, and then centrifuged at 3,000 rpm at 4° C. for 5 minutes. To the pellet, twofold volume (200μ‘) of a complete cracking buffer (8 M urea, 5% SDS, 40 mM Tris-HCl (pH 6.8), 0.1 mM EDTA, 145 mM 2-mercaptoethanol, 1 mM PMSF, 2 μg/ml aprotinin, 50 μg/ml leupeptin, 2 mM benzamidine, and 2 μg/ml pepstatin A) was added, and then the mixture was subjected to Vortex mixing and 150 μl of beads was added using a spatula. The mixture was allowed to stand at 70° C. for 10 minutes and centrifuged at 14,000 rpm at 4° C. for 5 minutes, and the supernatant was collected and subjected to SDS-PAGE (12.5% polyacrylamide gall. Western blotting using anti-LexA rabbit polyclonal antibody IgG as the primary antibody verified expression of NADE protein which gave a band in the position of 43 kDa.

(2) Transformation of yeast L40 with cDNA libraries derived from mouse embryo

The yeast L40 having the recombinant vector pBTM116-NADE obtained in (1) above was cultured in 1 L of SD-Trp medium placed in a 3 L flask with a baffle. Cultivation was started at 30° C. at the $OD_{600}$ of approximately 0.2, and continued to reach to $OD_{600}$ of 0.4 to 0.6.

The culture solution was transferred into a 50 ml tube and centrifuged at 3,000 rpm at room temperature for 5 minutes. The supernatant was removed, and the cell pellet was washed with distilled water 3 times and suspended in 8 m2 of 0.1 M lithium acetate/TE, and then the suspension was allowed to stand at room temperature for 10 minutes. The resulting cells was used as competent cells.

Separately, 100 μg of a cDNA library derived from mouse 9 day embryo, which was prepared with pVP16 vector (Glontech), and 20 mg (2 ml of 10 mg/ml solution) of denatured salmon sperm DNA were placed in a Falcon tube of 50 ml and well mixed with a Vortex mixer. To the resulting mixture, 8 ml of the competent cell solution was added, and the mixture was gently stirred. In addition, the resulting mixture of the competent cells and the DNA was added to a flask of 500 ml containing 60 ml of 40% PEG3350/0.1 M lithium acetate/TE. The mixture was well mixed, and cultured with shaking at 30° C. for 30 minutes. After addition of 7 ml of DMSO, the mixture was treated at 42° C. for 15 minutes (stirred every 5 minutes), and then cooled.

The cell solution was transferred into a tube of 250 ml and centrifuged at 3,000 rpm for 6 minutes, the supernatant was removed, and the cell pellet was washed with 600 ml of sterile distilled water once.

After centrifugation at 3,000 rpm for 5 minutes, the supernatant was removed, and then the cell pellet was suspended in 50 ml of YPD medium and inoculated in 2 flasks of 2 L containing 500 ml of YPD by each 25 ml portions. Cultivation was carried out with shaking at 30° C. for 1 hour. After centrifugation at 3,000 rpm at room temperature for 5 minutes, the supernatant was removed, and the cell pellet was washed with the same amount of sterile distilled water 4 times.

The cell pellet was suspended in 4.5 ml of sterile distilled water and spread over plates (150×15 mm) containing 0.5 ml of SD medium (-Trp, -Leu, -His) as 150 μl portions, and the plates were cultured at 30° C. for 3 to 5 days. The cell pellet diluted into appropriate amounts was spread over SD minimal medium (-Trp, -Lou) to determine transformation efficiency. 455 clones in total were isolated as colonies formed. Transformation efficiency was $7.7\times10^7$.

(3) β-gal assay

The transformed colony was inoculated by using a toothpick on a nylon membrane placed on a small plate of SD minimal medium (-Trp, -Leu), and cultured at 30° C. for 2 to 3 days. The membrane was torn off from the plate and placed on a floater of aluminium foil (about 30-seconds) cooled beforehand with liquid nitrogen, and frozen for 30 seconds. Then the membrane was immersed into liquid nitrogen together with the floater and frozen for 30 seconds. The membrane was taken out from liquid nitrogen using a pincette, and placed on a 3 MM filter paper so as to expose the colonies on the surface and then thawed.

The 3MM filter paper was cut into a round shape so as to fit the size of the small plate, and soaked with 3.2 ml of Z-buffer (60 mM $Na_2HP_4$, 40 mM $NaH_2PO_4$, 10 mM KCl, 1 mM $MgSO_4$) containing 50 μl of 25 mg/ml X-gal. The thawed membrane was placed on the filter using a pincette so as not to leave air bubbles, and then incubated at 37° C. for 30 minutes. After 1, 2, 4, 8 and 24 hours, color development was observed.

As a result, 436 clones with color development were observed in total.

(4) Curing test

In order to remove bait plasmid (pBTM116-NADE) from positive clones of the L40 strain, cultivation was conducted in SD liquid medium (-Leu) for 1 to 2 days, and single colonies were isolated using small plate medium containing the same amino acids. Then, the plate was replicated to SD medium (-Trp, -Leu) to give colonies not growing in -Trp medium.

As a result, 339 clones were isolated in total.

(5) Mating test

Mating was performed between clones losing pBTM116-NADE and having only library plasmid, and yeast for mating (NA87-11A, Mat α leu2 hisS trpl pho3 pho5) transformed beforehand with pBTM116-NADE, pBTM116-LaminC, pBTM116-CD40, pBTM116-Fas, pBTM116-Ras and pBTM116-TNFRII, respectively. The yeast clone losing pBTM116-NADE and having only library plasmid was cultured with shaking in SD liquid medium (-Leu), and pBTM116-NADE/NA87-11A, pBTM116-LaminC/NA87-11A, pBTM116CD40/NA87-11A, pBTM116-Fas/NA87-11A, pBTM116-Ras/NA87-11A, and pBTM116-TNFRII/NA87-11A were cultured with shaking in SD liquid medium (-Trp), respectively, at 30° C. until $OD_{000}$>1.0, and both clones are subjected to mating in 100 μl of YPD using a 96-well plate at 30° C. for 4 to 8 hours.

After the mating, each clone was spotted on SD plates (-Trip, -Leu) by 6 to 10 μl portions and cultured at 30° C. for 2 days. In addition, whether or not the resulting clones express a protein specifically binding to NADE was examined using two reporter genes, His and β-gal.

As a result, a protein specifically binding to NADE was found and lob clones in total were obtained as those judged to be positive in the His selection and β-gal assay.

Example 2

Structural Analysis of NADE Binding Protein Molecules Identified by Yeast Two-hybrid Method As to 96 clones among the positive obtained in Example 1, cDNAs derived from the library that the yeast had were collected, and their base sequences were determined.

The yeast culture solution was first centrifuged at 3,000 rpm for 5 minutes and the supernatant was removed, and then the pellet was suspended in 500 μl of water and transferred into a tube of 1.5 ml. After centrifugation at 15,000 rpm for 5 seconds, the supernatant was removed. To the residue, 150 μl of the SZB aqueous solution (1 M sorbitol, 100 mM sodium citrate, 50 mM EDTA, and 8 μl/ml or 2-mercaptoethanol; further added with 3 mg/ml of ZYMOLYASE (Seikagaku Kogyo; Code 12049; Lot No 10971) just before its use) was added, and the mixture was suspended and then allowed to stand at 30° C. for 30 minutes with mixing by turning upside down every 5 minutes. The SDS/TE solution (0.1 M Tris-HCI (pH 8.0), 2% SDS) (160 μg) was added, and the mixture was subjected to Vortex mixing and treated at 65° C. for 5 minutes. 5 M potassium acetate (160 μl was added, and the mixture was subjected to Vortex mixing and allowed to stand on ice for 30 minutes. After centrifugation at 15,000 rpm at 4° C. for 15 minutes, a portion of 300μl of the supernatant was transferred into a new tube of 1.5 ml, and then the portion was added with 100 μl of 10 M ammonium acetate and 1 ml of ethanol and allowed to stand at −20° C. for 10 minutes. The operation of further centrifugation and standing was repeated twice, and the pellet was finally washed with 70% ethanol and then dissolved in 30 μl of water to give a plasmid solution.

The plasmid above was transformed into *E. coli* using electroporation (applying pulses to the mixture of *E. coli* and the plasmid at 1.7 kV, 25μF and 200 Ω and then the cells were cultured at 37° C. for 1 hour), and the plasmid was collected from the resulting transformant by alkali method. Using the collected plasmid, the base sequences of the positive clones obtained in Example 1 were determined by a conventional method and compared with the database. As a result of comparison with the database (NCBI's sequence similarity tool), clones having homology to the following base sequences were identified. The numbers in parentheses indicate those of clones obtained.

Mus 14-3-3 eta (1)
mus 14-3-3 beta (1)
Mus 16-3-3 epsilon (4)
NIK (Nek interacting kinase) (4)
Mus EST AA294707 (5)
Hum Desmoplakin I (3)
Hum elF4G (3)
Mus nuclear autoantigen sperm protein (3)
hum KIAA 0192 (3)
Mus M2 type pyrubate kinase (3)
Hum TSC1 (2)
Mus laminin B1 (2)
Mus EST AA299218 (2)
Hum protein regulating cytokinesis 1(2)

Mus NADE (1)
Mus endophilin II (1)
Hum Huntingtin binding protein 1(HIP1 ) (1)
Rat protein tyroaine phosphatase TD 14 (1)
Mus CAG repeat mRNA partial U20888 (1)
mus TRF1 (1)
Hum PTAC97 (1)
Mus putative transcription factor (1)
Hum rab3(GAP reguratory domain (1)
Hum Ran GTP B.P. (1)
HUM RB B.P.II (1).
Mus ret finger protein 1(REFl) (1)
Set alpha isoform (1)
Hum splicing factor SRp55-3 (1)
Hum SW1/SNF complex 170kD subunit (1)
Hum tax 1 B.P. (1)
Mus casein kinase II (1)
Mus cdr 2 (1)
Mus fat facets homologue (Fam) (1)
B.Tra guanine nucleotide exchanging P. (1)
Mus KIF3 (1)
Hum Lowe's oculocerebrorenal syndrome (OCRL) (1)
Hum LZTR-1 leucine zipper,ttk DiGeorge (1)
Mus Mov-34 (1)
Ratt myosin heavy chain (1)
Hum EF1 delta leu.zip contain G-nucleotide ex.(1)
Hum auto antigen (1)
Rat beta adaptin mRNA, complete cds (1)
Rat beta spectrin (1)
Hum DOCK 180 (1)
Hum Dynactin 50k subunit (1)
hum EF1 delta (1)
myotonic dystrophy kinase-related Cdc42(kinase MRCK-beta(1)
Mus EST AA967322 (1)
mus EST AU036250 (1)
Mus EST C85116 (1)
Mus EST W75029 (1)
Mus EST (1)
Mus EST 032345 (1)
Mus EST AA207590 (1)
Mus EST AA277260 (1)
Mue EST AA413882 (1)
Mus EST AA717789 (1)
mus EST AA755361 (1)
Hum KIAA0161 (1)
Hum KIAA0181 (1)
Hum KIAA05641CDC42 B.P. (1)
Unknown (7)

Among the clones obtained, protein molecules considered to be especially important include the following five proteins. Information of these proteins will be shown below.

(1) 14-3-3 Protein
a) 14-3-3 E (255 amino acids)
Monoisotonic molecular weight=29,155.4130
b) 14-3-3 β (246 amino acids)
Monoisotonic molecular weight=28,078.8437
c) 14-3-3 η (246 amino acids)

Monoisotonic molecular weight=28,194.0212

It is considered that 14-3-3 protein exists as a hetero- or homo-dimer and binds to various proteins as shown below, and that the protein participates in regulation of activity and protein localization.

(Proteins reported to be bound by 14-3-3 protein)
c-Raf-1/A-Raf/Cdc25a/Cdc25b/Cdc25c/PKC-epsilon/PCTAIRB-2/
Tyr hydroxylase/ Tryp hydroxylase/A20/BAD/Cbl/PKC gamma/
IRS-1/BCR/K8kwratin/c-fes (2) NIK (Nck interacting kinase [mouse]/HGK [human]) (1,233 amino acids)
Molecular weight=140,515

NIK/HGK functions as an upstream factor MAPKKKK in MAPK cascade to regulate the activity of JNK or P38MAPK through phosphorylation of MEKK and TAK. Recently, different groups have reported that JNK participates in the apoptosis regulation signal mechanism, suggesting that NIK/HGK participates in apoptosis induced by NGF/$p75^{NTR}$, (3) P33ING1 (294 amino acids)
Molecular weight=33,273.84

P33ING1 is a candidate of a cancer repressor gene mapped in 18q34, and highly expressed in aged fibroblasts. Binding to p53 leads to participation in transcription induction of p21WAF1, and high expression induces G1 arrest. Apoptosis relating to cell cycle may possibly be regulated through ING2. The clone obtained was relative to p33ING with homology.

(4) eIF4G Protein (translation initiator) (1,560 amino acids)

eIF4G binds to proteins connecting to the 3'- and 5'-terminals of mRNA (PABP: poly A binding protein, eIF4E: binding to CAP structure) to capture mRNA, and gather ribosomes and lead to translation initiation. Translation regulation may possibly control apoptosis through NADE/eIF4G.

(5) Huntingtin binding protein 1(HIP1) (914 amino acids)
Molecular weight=102,317.03

This protein is expressed specifically in the cerebrum and cerebellum (no expression of HIP1 protein in skeletal muscle, heart, testis, kidney, spleen, liver, and lung), and binds to huntingtin which is a causal gene product for Huntington's chorea. HIP1 has homology to Sla2p and Sla2c of yeast *S. cerevisiae* (cytoskeltal-associated protein) and ZK370.3 of C. elegans, suggesting that HIP1 participates in apoptosis control through regulation of cytoskeleton formation.

Example 3

Binding of NADE Protein with 14-3-3 Protein in vivo

NADE protein expressed in mammal cultured cells was verified to bind to 14-3-3 by an immune precipitation experiment.

To 293T cells derived from human fetal kidney, a mixed solution was added dropwise which was prepared by mixing solution A of expression vector (mNADE/pcDNA3.1(-) Hismycl) containing 500 μl of OptiMEM and 10 μl or 1 mg/ml NADEcDNA with solution B of 500 μl of OptiMEM and 30 μl of lipofectamine (BRL) and further adding 4 ml of OptiMEM. The mixture was cultured under 5% $CO_2$ at 37° C. for 4 hours. The solution was removed, and 10 ml of complete medium was added. Cultivation was continued under 6% $CO_2$ at 37° C. for transfection of the cells.

After 48 hours from the transfection, the cells were collected and washed twice with 10 ml of PBS and once with 1 ml of PBS. The cells were added with 1 ml of lysis buffer (150 mM NaCl, 1% Triton X200, 20 mM Tris-HCl (pH 7.2), 1 mM EDTA), and centrifuged at 15,000 rpm at 4° C. for 30 minutes.

To the protein solution of the cell supernatant obtained above (0.15 ml of 2 mg/ml solution), 1$\mu$g of anti-NADE antibody and 20 $\mu$l of Protein G Sepharose (Amersham Pharmacia) equilibrated beforehand with lysis buffer were added.

The immune precipitate was separated by performing SDS-PAGE (12.5% polyacrylamide, 200 V, 1 hour) in a conventional manner, and subjected to Western blotting. The resulting membrane was reacted with anti-14-3-3 antibody (Santa Cruz) as the primary antibody, and then with 4,000-fold diluted solutions of horseradish peroxidase-binding goat anti-mouse IgG and horseradish peroxidase-binding goat anti-rabbit IgG (BioRad) as the secondary antibodies, respectively, and then subjected to detection using ECL detection kit (Amersham Pharmacia).

As a result, a specific band was detected in a lane in which anti 14-3-3 antibody was reacted with the immune precipitation fraction of the protein extract which was derived from cells transformed with expression vector containing NADEcDNA.

In a similar manner, by using a cell extract of ES cells (D3) derived from mouse intraembryonic cell aggregate (containing endogenous NADE), protein molecules bound by adding NADE antibody end Protein G Sepharose was subjected to SDS-PAGE and Western blotting in a conventional manner. As the primary antibody, anti-14-3-3 antibody (Sant Cruz) was used, and as the secondary antibodies, 4,000-fold diluted solutions of horseradish peroxidase-binding goat anti-mouse IgG and horseradish peroxidase-binding goat anti-rabbit IgG (BioRad) were used. Detection was NADE by using ECL detection kit (Amersham Pharmacia). As a result, a specific band was detected.

The aforementioned results showing that 14-3-3/NADE forms a complex in 293T cells and ES cells (D3) indicate that 14-3-3/NADE forms a complex also in vivo.

Example 4

Binding of NADE Protein with NIK/HGK Protein in vivo

NADE protein expressed in mammal cultured cells was revealed to bind to NIK/HGK by an immune precipitation experiment in a similar manner to that in Example 3.

293T cells were cultured overnight, and transformed by calcium chloride method by adding 10 $\mu$g/plate of recombinant vector for NADE expression (pcDNA2.1(NADE-MycHis) and 10 $\mu$g/plate of expression recombinant vector containing full length human NIK (HGK) connected with FLAG. The transformed cells were collected and washed, and a cell extract was prepared. To the cell extract, anti-FLAG antibody (using 1 $\mu$g of antibody per plate of the cell extract) and 20 $\mu$l of Protein G Sepharose (Amersham Pharmacia) were added.

The immune precipitate was separated by performing SDS-PAGE (10% polyacrylamide, 200 V 1 hour) and subjected to Western blotting to a nylon membrane in a conventional manner. The resulting membrane was soaked in the primary antibody solution (1 $\mu$g/ml of anti-NADE antibody) for the reaction, and after ,washing, the membrane was then soaked in the secondary antibody solution (3,000-fold diluted solution of horseradish peroxidase-binding goat anti-rabbit IgG (BioRad)) for the reaction. Detection was NADE by the ECL method.

As a result, a specific band was detected when detection was NADE to the immune precipitation fraction of the protein extract, which was derived from cells transformed with expression vector containing NADEcDNA and expression recombinant vector containing full length NIK/HGK connecting to FLAGby, by using anti-NADE antibody as the primary antibody. The results indicate that NIK/NADE forms a complex also in vivo.

Example 5

Promotion of the Binding of NADE Protein with 14-3-3 Protein by Nerve Growth Factor (NGF)

It was revealed that the binding of NADE protein with 14-3-3 protein was promoted by nerve growth factor (NGF).

PCNA cells cultured in serum minus medium for 12 hours (70% confluent, 10 cm plate) was collected and suspended in 9 ml of serum minus medium. The cells were added with NGF so as to adjust the final concentration to 10 ng/ml, and incubated for 2 hours. Then, a cell extract was prepared. To the cell extract, anti-NADE antibody (1 $\mu$g of 200 $\mu$g/ml solution) and 10 $\mu$l of Protein G Sepharose (Amersham Pharmacia) were added. The immune precipitate was subjected to SDS-PAGE and Western blotting, and analyzed by using anti-14-3-3 protein antibody to the primary antibody in a similar manner to those in Examples 3 and 4. As a result, 143-3 was detected in response to NGF stimulation, The results indicate that the binding of the 14-3-3/NADE complex is involved in the information transfer system of the NGF/$p^{75NTR}$ complex.

Sequence Listing

<110> The Institute of Physical and Chemical Research (RIKEN)
<120> NADE Binding Proteins
<130>
<160> 2
<210> 1
<211> 29
<212> DNA
<213> Synthetic DNA
<400>1
atggatcctc atggccaatg tccaccagg 29
<210> 2
<211> 32
<212> DNA
<213> Synthetic DNA
<400> 2
atctcgagtc aaggcataag geagaattca to 32

What is claimed is:

1. A method for screening a candidate medicament for treatment and/or prevention of an apoptosis-associated disease which comprises adding an agent to be tested, NADE (p75NTR-associated cell death executer) and an apoptosis related protein which binds to NADE, in a system, and detecting and determining the effect on the binding between NADE and an apoptosis related protein which binds to NADE in the presence of said agent, wherein the agent is selected as a candidate medicament when the agent inhibits or increases the binding between NADE and an apoptosis related protein which binds to NADE and wherein the apoptosis related protein which binds to NADE is chosen from the group consisting of 14-3-3 protein, NIK/HGK protein, P33 ING1, protein, eIF4G protein and Hungtington-binding protein 1.

* * * * *

UNITED STATES PATENT AND TRADEMARK OFFICE

CERTIFICATE OF CORRECTION

PATENT NO. : 6,939,679 B1
DATED : September 6, 2005
INVENTOR(S) : T. Sato et al.

It is certified that error appears in the above-identified patent and that said Letters Patent is hereby corrected as shown below:

Title page,
Item [56], References Cited, FOREIGN PATENT DOCUMENTS,
"95/51544" should be -- 95/31544 --.
Item [57], ABSTRACT,
Line 3, "apoptosis associated" should be -- apoptosis-associated --.
Line 4, "76" should be -- 75 --.

Column 14,
Line 54, "executer" should be -- executor --.
Line 64, before "protein" delete ",".
Line 64, "Hungtington" should be -- Huntington --.

Signed and Sealed this

Eighteenth Day of April, 2006

JON W. DUDAS
*Director of the United States Patent and Trademark Office*